US011419707B2

(12) United States Patent
Atiya et al.

(10) Patent No.: US 11,419,707 B2
(45) Date of Patent: Aug. 23, 2022

(54) DIGITAL DENTAL TRAY FOR 3D MODEL GENERATION

(71) Applicant: Align Technology, Inc., San Jose, CA (US)

(72) Inventors: Yossef Atiya, Maccabim (IL); Avi Kopelman, Palo Alto, CA (US); Erez Lampert, Rehevot (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/086,208

(22) Filed: Oct. 30, 2020

(65) Prior Publication Data

US 2021/0045852 A1 Feb. 18, 2021

Related U.S. Application Data

(63) Continuation of application No. 15/814,244, filed on Nov. 15, 2017, now Pat. No. 10,849,721, which is a
(Continued)

(51) Int. Cl.
*A61C 9/00* (2006.01)
*A61B 1/253* (2006.01)
(Continued)

(52) U.S. Cl.
CPC .......... *A61C 9/006* (2013.01); *A61B 1/00009* (2013.01); *A61B 1/00016* (2013.01);
(Continued)

(58) Field of Classification Search
CPC combination set(s) only.
See application file for complete search history.

(56) References Cited

U.S. PATENT DOCUMENTS 6,589,054 B2 7/2003 Tingley et al.
8,520,925 B2 8/2013 Duret
(Continued)

FOREIGN PATENT DOCUMENTS

DE 112012005886 T5 11/2014
WO 9731293 A1 8/1997
WO 2008064904 A1 6/2008

OTHER PUBLICATIONS

Schechner et al., "Depth from Defocus vs. Stereo: How Different Really Are They?" International Journal of Computer Vision, 39(2), Sep. 2000, pp. 141-162; http://webee.technion.ac.il/~yoav/publications/dfdstereot2a.pdf.
(Continued)

*Primary Examiner* — Md N Haque
(74) *Attorney, Agent, or Firm* — Lowenstein Sandler LLP

(57) ABSTRACT

A system comprises a dental tray comprising an array of fixed focus cameras, wherein each fixed focus camera of the first array of fixed focus cameras has a fixed position and orientation relative to one or more other fixed focus camera of the array of fixed focus cameras. The system further comprises a processing device to receive a plurality of images generated by the array of fixed focus cameras, stitch the plurality of images together based on calibration data specifying predetermined image stitching parameters for combining the plurality of images, wherein the predetermined image stitching parameters are based on predetermined fixed relative positions and orientations of fixed focus cameras from the array of fixed focus cameras, and generate a three-dimensional model of a plurality of teeth based on the stitched plurality of images.

20 Claims, 8 Drawing Sheets

Related U.S. Application Data continuation of application No. 14/656,523, filed on Mar. 12, 2015, now Pat. No. 9,844,426.

(51) Int. Cl.
| | |
|---|---|
| *A61B 1/00* | (2006.01) |
| *A61B 1/06* | (2006.01) |
| *A61B 5/00* | (2006.01) |
| *A61B 5/107* | (2006.01) |
| *A61B 1/015* | (2006.01) |
| *A61B 1/04* | (2006.01) |
| *A61B 1/12* | (2006.01) |
| *A61B 1/24* | (2006.01) |
| *A61B 5/01* | (2006.01) |

(52) U.S. Cl.
CPC ...... *A61B 1/00142* (2013.01); *A61B 1/00181* (2013.01); *A61B 1/00193* (2013.01); *A61B 1/015* (2013.01); *A61B 1/04* (2013.01); *A61B 1/06* (2013.01); *A61B 1/0684* (2013.01); *A61B 1/126* (2013.01); *A61B 1/128* (2013.01); *A61B 1/24* (2013.01); *A61B 1/253* (2013.01); *A61B 5/0088* (2013.01); *A61B 5/1077* (2013.01); *A61B 5/1079* (2013.01); *A61B 5/4547* (2013.01); *A61C 9/0006* (2013.01); *A61B 5/01* (2013.01); *A61B 2560/0242* (2013.01); *A61B 2562/043* (2013.01); *A61C 2204/002* (2013.01)

(56) References Cited

U.S. PATENT DOCUMENTS

| | | | |
|---|---|---|---|
| 9,199,574 | B2 | 12/2015 | Pierce |
| 2002/0055082 | A1 | 5/2002 | Durbin et al. |
| 2003/0219148 | A1* | 11/2003 | Scharlack ................ G06T 7/30 382/128 |
| 2005/0048444 | A1 | 3/2005 | Creamer |
| 2005/0143625 | A1 | 6/2005 | Whitmore, III et al. |
| 2006/0141416 | A1* | 6/2006 | Knutson ............. A61C 9/0006 433/37 |
| 2007/0015112 | A1* | 1/2007 | Hochman ............ A61B 8/546 433/215 |
| 2007/0020584 | A1 | 1/2007 | Madray |
| 2007/0248930 | A1 | 10/2007 | Brawn |
| 2008/0063998 | A1 | 3/2008 | Liang et al. |
| 2008/0090198 | A1 | 4/2008 | Liang et al. |
| 2008/0280260 | A1 | 11/2008 | Belikov et al. |
| 2009/0080766 | A1 | 3/2009 | Daxauer et al. |
| 2010/0009313 | A1 | 1/2010 | Kushner |
| 2010/0036535 | A1 | 2/2010 | Feine et al. |
| 2010/0239136 | A1 | 9/2010 | Gandyra et al. |
| 2011/0076636 | A1 | 3/2011 | Wolff et al. |
| 2011/0130627 | A1* | 6/2011 | McGrail ............... A61B 1/267 600/109 |
| 2012/0064477 | A1 | 3/2012 | Schmitt |
| 2012/0088971 | A1* | 4/2012 | Napier ............. A61M 16/0493 600/109 |
| 2013/0027516 | A1* | 1/2013 | Hart ................... A61B 1/00193 348/45 |
| 2013/0108981 | A1 | 5/2013 | Duret |
| 2013/0323673 | A1 | 12/2013 | Hakomori et al. |
| 2014/0146142 | A1 | 5/2014 | Duret et al. |
| 2014/0212841 | A1 | 7/2014 | Nguyen et al. |
| 2014/0272765 | A1 | 9/2014 | Andreiko et al. |
| 2014/0277665 | A1 | 9/2014 | Fisker |
| 2015/0064641 | A1 | 3/2015 | Gardner |
| 2015/0079534 | A1* | 3/2015 | Tsuji ................ A61C 9/0053 433/29 |
| 2016/0242692 | A1 | 8/2016 | McAuliffe et al. |

OTHER PUBLICATIONS

Kapusta, Roman, "Scene reconstruction using structured light," Slovak University of Technology Bratislava Faculty of Elecrical Engineering and Information Technology, Bratislava, Slovakia, 2003, 6 pages, Downloaded Mar. 13, 2015 from http://www.cescg.org/CESCG-2003/RKapusta/paper.pdf.

Greengard et al., "Depth from diffracted rotation," Optics Letters, vol. 31, No. 2, Jan. 15, 2006, pp. 181-183; http://cgm.technion.ac.il/Computer-Graphics-Multimedia/Publications/Papers/2006/2006_Depth_from_diffracted_rotation.pdf.

* cited by examiner

DIGITAL DENTAL TRAY FOR 3D MODEL GENERATION

RELATED APPLICATIONS

The present application is a continuation of U.S. patent application Ser. No. 15/814,244, filed Nov. 15, 2017, which is a continuation of U.S. patent application Ser. No. 14/656,523, filed Mar. 12, 2015, both of which are incorporated by reference herein.

TECHNICAL FIELD

Embodiments of the present invention relate to the field of intraoral scanning and, in particular, to a system and method for using a digital dental tray for intraoral scanning.

BACKGROUND

In prosthodontic procedures designed to implant a dental prosthesis in the oral cavity, the dental site at which the prosthesis is to be implanted may be measured accurately and studied carefully, so that a prosthesis such as a crown, denture or bridge, for example, can be properly designed and dimensioned to fit in place. A good fit, for example, enables mechanical stresses to be properly transmitted between the prosthesis and the jaw and minimizes infection of the gums via the interface between the prosthesis and the dental site.

Some procedures call for removable prosthetics to be fabricated to replace one or more missing teeth, such as a partial or full denture, in which case the surface contours of the areas where the teeth are missing may be reproduced accurately so that the resulting prosthetic fits over the edentulous region with even pressure on the soft tissues.

In some practices, the dental site is prepared by a dental practitioner, and a positive physical model of the dental site is constructed. Alternatively, the dental site may be scanned or otherwise imaged to provide three-dimensional (3D) data of the dental site. In either case, the virtual or real model of the dental site may be sent to a dental lab that manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry may need to be altered to avoid the collision. Further, if the area of the preparation containing a finish line lacks definition, it may not be possible to properly determine the finish line and thus the apical edge of the coping may not be properly designed. Indeed, in some circumstances, the model is rejected and the dental practitioner then re-images the dental site, or reworks the preparation, so that a suitable prosthesis may be produced.

In orthodontic procedures, it can be important to provide a model of one or both dental arches and/or a jaw of a patient. Where such orthodontic procedures are designed virtually, a virtual model of the oral cavity is also beneficial. Such a virtual model may be obtained by imaging the oral cavity directly, or by producing a physical model of the dentition, and then imaging the model with a suitable imaging device.

BRIEF DESCRIPTION OF THE DRAWINGS

The present invention is illustrated by way of example, and not by way of limitation, in the figures of the accompanying drawings.

DETAILED DESCRIPTION

Described herein is a method and apparatus for generating a three-dimensional (3D) model of a patient's teeth using a dental tray with 3D optical imaging elements (also referred to herein as a digital dental tray). In one embodiment, a dentist or other dental practitioner may generate a model of a patient's teeth by taking an impression of a dental site using an elastomeric impression material (e.g., as polyvinyl siloxanes (PVS) or polyethers (PE)) or an alginate impression material, placed in a conventional dental tray. The resulting impression may be used as a negative to generate a physical model that is scanned into a digital 3D model of the dental site. In another embodiment, a dental practitioner may use a wand-shaped intraoral scanner to capture the patient's dental topography by consecutively scanning the wand the patient's teeth. Both techniques for capturing a patient's dental topography may have drawbacks in some situations. The dental tray discussed in embodiments herein is capable of capturing a patient's dental topography without the potential drawbacks of the other discussed techniques.

In one embodiment, the dental practitioner uses a digital dental tray that does not use an impression material to create a model of a patient's teeth. The digital dental tray includes an array of 3D optical imaging elements with overlapping fields of view to capture the topography of a plurality of the patient's teeth, even all of the patient's teeth, at one time. By capturing images of all of the patient's teeth at one time, the amount of time needed to capture the topography of the dental site may be reduced. This may be convenient for both the practitioner and the patient, and may improve practitioner throughput. In particular, discomfort associated with long impression times using physical impression materials or wand-shaped scanners may be reduced. Further, such reduction in the capture time increases the accuracy and reliability of the capture. The reliability of the capture of dental site images in some embodiments may also be increased by the lack of moving parts of the dental tray and the fixed position of the 3D optical imaging elements with respect to each other.

Figure 1:
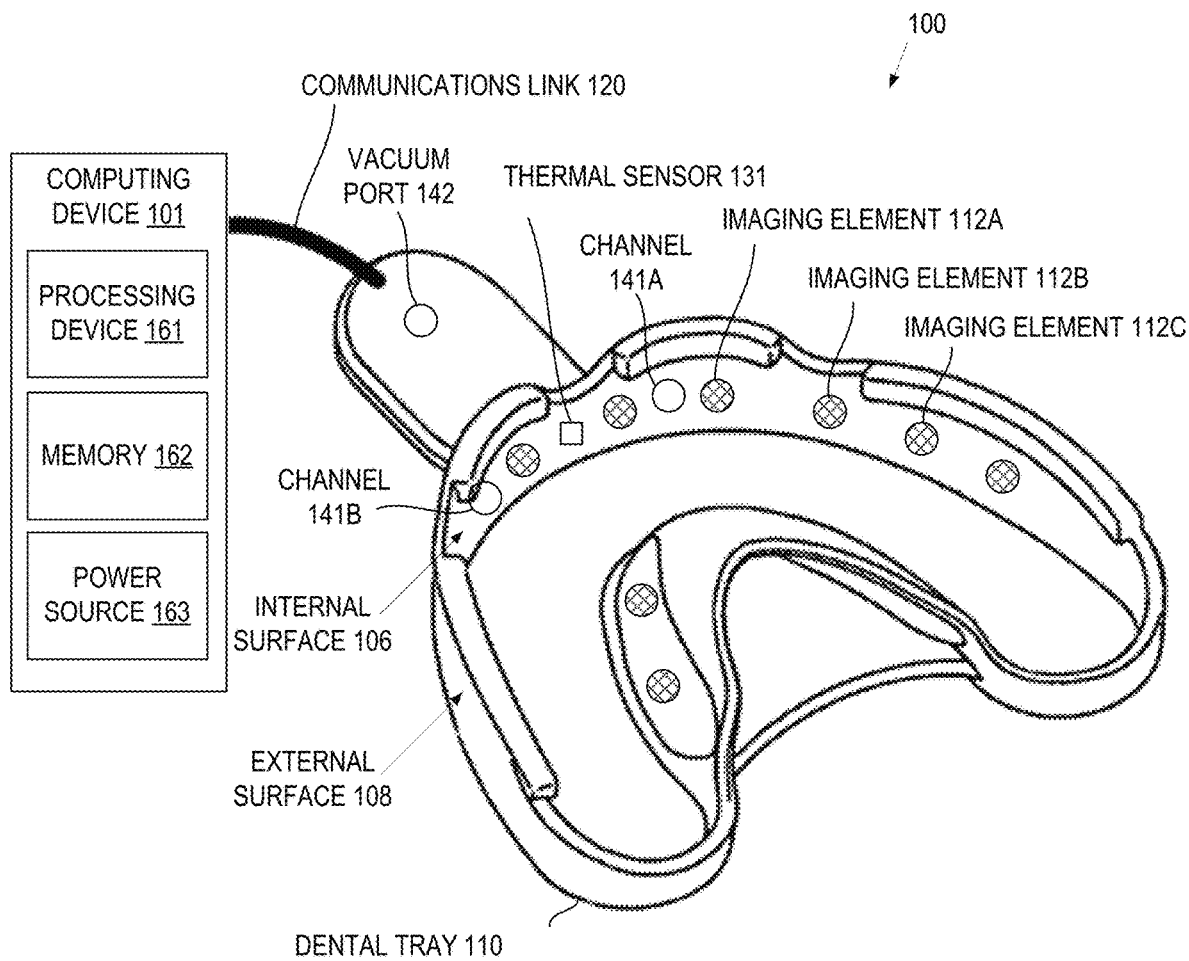
FIG. 1 illustrates one embodiment of a system for performing intraoral scanning using a dental tray with embedded imaging elements.

FIG. 1 illustrates one embodiment of a system 100 for performing intraoral scanning (and potentially intraoral modelling) using a dental tray 110 (e.g., a digital dental tray) with embedded imaging elements 112A-112C. The system 100 includes a dental tray 110 coupled by a communication link 120 to a computing device 101. The dental tray 110 includes an array of imaging elements 112A-112C to generate images of one or more teeth of a patient that can be used to generate a 3D model of the patient's mouth (e.g., of a jaw and/or teeth of the patient).

The dental tray 110 is shaped to at least partially surround one or more teeth of the patient. In particular, the dental tray 110 includes an internal surface 106 that defines a tray cavity into which the patient's teeth are positioned. In one embodiment, the dental tray 110 may be shaped (as illustrated in FIG. 1) to at least partially surround both the upper teeth and the lower teeth of the patient. This may enable the imaging elements 112A-112C of the dental tray 110 to create images usable to create a full mouth model of a patient dental site, including jaw, teeth, bite information, and so on. In another embodiment, the dental tray 110 may be shaped to at least partially surround only the upper teeth or only the lower teeth at any one time. In such an embodiment, the system 100 may be used to successively model the upper teeth in the maxilla (upper jaw) and then the lower teeth in the mandible (lower jaw) by first placing the dental tray 110 over the upper teeth and generating a first set of images and then placing the dental tray 110 over the lower teeth and generating a second set of images. In another embodiment, the dental tray 110 may be shaped to surround a quadrant portion of the patient's teeth or any or section including two or more teeth. In such an embodiment, the dental tray 110 may be positioned at a first location on an upper or lower jaw to take a first set of images, repositioned to a second location on the upper or lower jaw to take a second set of images, and so on until all desired portions of the patient's upper and/or lower jaw (and associated teeth) have been imaged.

The dental tray 110 includes an array of imaging elements 112A-112C to generate images of the teeth of the patient, and in some instances to generate images of the jaw to which the teeth are attached. The imaging elements 112A-112C may be three-dimensional (3D) optical imaging elements that generate images (e.g., 3D images) that may be used to generate a 3D model of the teeth of the patient. The imaging elements 112A-112C may be embedded in the dental tray 110 or otherwise attached to the dental tray 110, each positioned to have a field of view of a portion of one or more teeth, facing the one or more teeth when the dental tray is positioned in a patient's mouth over the patient's teeth. As described in detail below, the imaging elements 112A-112C may be spaced and positioned such that each imaging element 112A-112C generates images of at least a portion of one or more first teeth in a field of view of the imaging element 112A-112C that overlaps with at least a portion of one or more second teeth in a field of view of another imaging element 112A-112C. Although three imaging elements 112A-112C are labelled in FIG. 1, it is to be appreciated that the dental tray 110 may include any number of imaging elements 112A-112C.

Each imaging element 112A-112C may generate images of the subset of the teeth in the field of view of the imaging element 112A-112C. Each imaging element 112A-112C may include one or more cameras and/or one or more illumination devices. In one embodiment, each imaging element 112A-112C includes a stereoscopic camera pair and an illumination device and generates a pair of images from slightly different angles. The pair of images may be used to generate a 3D model or image of the section of teeth where the fields of view of the pair of images overlap. Such an embodiment is described more fully with reference to FIG. 2A. In another embodiment, each imaging element 112A-112C includes a fixed focus camera and an illumination device and a 3D model may be generated using depth from defocus principles. Such an embodiment is described more fully with reference to FIG. 2B. In another embodiment, each imaging element 112A-112C includes a camera and a structured light projector and may be used to generate a 3D model using triangulation principles and/or a comparison of a known pattern of the structured light verses a captured pattern of the structured light as reflected off of the teeth of the patient. Such an embodiment is described more fully with reference to FIG. 2C.

The dental tray 110 (and the various components thereof, such as the imaging elements 112A-112C or their subparts) may be connected to computing device 101 via a communications link 120. The communications link 120 may be a wired link between the dental tray 110 and the computing device 101, as shown. Alternatively, the communications link 120 may be a wireless connection that is established between the dental tray and computing device 101 via a wireless module (not shown) of the dental tray. The communications link 120 may allow for the transmission of a large amount of data generated by each scan. In one embodiment, approximately 50 stereo camera pairs, each capturing 4 frames, generates approximately 400 color frames that may be transmitted over the communications link 120. Alternatively, up to approximately 50 or more fixed focus cameras or traditional cameras may each capture around 4 frames in an embodiment, resulting in approximately 200 frames that are transmitted. The communications link 120 may be a two-way communications link that allows communication from the dental tray 110 to the computing device 101 and from the computing device 101 to the dental tray 110. The computing device 101 may provide control or instructions to the dental tray 110 via the communications link 120 and receive feedback or image data from the dental tray 110 via the communications link 120.

The computing device 101 may include a processing device 161 for controlling the dental tray 110 and/or for processing data received from the dental tray 110. The computing device 101 may additionally include a memory 162 to store received data, such as image data, and a power source 163 for providing power to the dental tray 110. Alternatively, the dental tray may include its own power source, such as a rechargeable battery. For example, the dental tray 110 may include a standard or rechargeable battery if it does not have a wired link to computing device 101. The computing device 101 may also include other components, such as those described below with respect to FIG. 7.

In one embodiment, the dental tray 110 is shaped to at least partially surround a subset of patient teeth such that the teeth are confined in a relatively enclosed volume. The teeth may therefore be isolated from the humid environment of the intraoral cavity by the dental tray 110 such that fog does not form on the internal surface 106 of the dental tray 110. Alternatively, the dental tray 110 may not isolate the teeth from the humid environment of the intraoral cavity. Accordingly, the imaging elements 112A-112C may have a tendency to fog over time in some embodiments. However, the dental tray 110 may further include a thermal sensor 131 configured to sense an environment (e.g., temperature) of the dental tray 110. The thermal sensor 131 may communicate the sensed temperature via the communications link 120 to the computing device 101. The computing device 101 (or the processing device 161 thereof) may control the temperature of the environment of the dental tray 110 based on the sensed temperature to defog the dental tray 110, preventing the generation of fog on the dental tray 110 or removing fog that is present. Alternatively, dental tray 110 may include a controller (not shown), which may receive the temperature measurements and determine settings for the imaging elements 112A-112C and/or heating elements therefrom. The controller may then adjust the settings of the imaging elements 112A-112C and/or heating elements to prevent the generation of fog and/or remove accumulated fog. The controller may be a programmable logic control, system on a chip (SoC), field programmable gate array, microprocessor, and/or other processing device. The processing device 161 or controller may control the temperature by controlling one or more illumination device of the imaging elements 112A-112C or any another heating element (also referred to as a heat generator) that generates heat in the environment of the dental tray 110. In one embodiment, where each camera pair has its own LED light illumination unit that consumes approximately 0.25 watts, the total power dissipation, assuming all cameras work in parallel, may be 54 times this, or approximately 13.5 watts. Some of this generated heat may be used to defog the dental tray 110. In one embodiment, the processing device 161 or controller controls the temperature by preheating the dental tray 110 to approximately body temperature prior to insertion of the dental tray into the mouth of the patient.

The dental tray 110 may have one or a plurality of channels 141A-141B through the dental tray 110 between the internal surface 106 of the dental tray and a vacuum port 142 of the external surface 108. The channels 141A-141B may be continuous spaces defined by a tubular inner surface connecting the internal surface 106 and the vacuum port 142 of the external surface 108. A disposable and transparent contamination control film (not shown) may be disposed over the internal surface 106 of the dental tray 110 prior to insertion of the dental tray into the mouth of the patient. The film may be shaped to cover the dental tray 110 or just a portion of the dental tray 110 and prevent contamination of the dental tray 110 (or a portion thereof) by exposure of the dental tray to the intraoral cavity of the patient.

The contamination control film may be thin and optically clear such that the film does not impact the imaging quality or geometry of images captured by the imaging elements 112A-112C. The film may be composed of polyvinyl chloride, polyethylene, or any other transparent material. A vacuum machine may be coupled to the vacuum port 142 to remove air from the channels 141A-141B and adhere the film to the internal surface 106 of the dental tray. In one embodiment, a tube connected to a vacuum machine is coupled to the vacuum port 142 to create a slight vacuum. The vacuum should be strong enough to cause the film to adhere to the dental tray 110, but not strong enough to deform the film or to generate holes, tears or rips in the film. The film may alternatively be adhered to the internal surface 106 by surface tension, static electricity, or any other method. Once imaging of a dental site is complete, the film may be removed and disposed of.

In one embodiment, the dental tray 110 is composed of a translucent or opaque material that can withstand disinfecting autoclave temperatures. In one embodiment, the dental tray has a rigid or semi-rigid body that may include metal and/or plastic. The imaging elements and other components may be attached to or integrated into this body. The body may be cast into (encapsulated in) a translucent material, such as polypropylene or another plastic, that can withstand disinfecting autoclave temperatures. The imaging elements 112A-112B and other components may be embedded within the dental tray 110, and may also be constructed to withstand autoclave temperatures. The dental tray 110 and its components may be composed of autoclavable materials that are not damaged or deformed by temperatures between approximately 100° C. and 150° C.

Figure 2A:
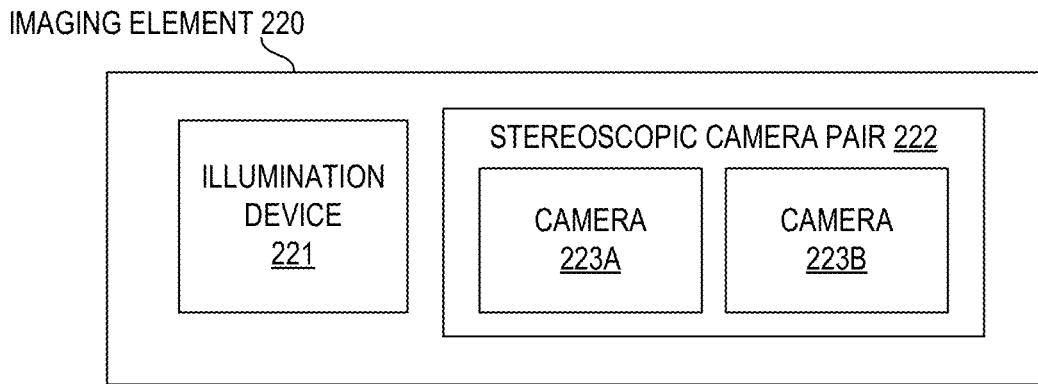
FIG. 2A illustrates one embodiment of an imaging element for generating images using a stereoscopic camera pair.

FIG. 2A illustrates one embodiment of an imaging element 220 for generating images using a stereoscopic camera pair 222. The imaging element 221 may be one of the array of imaging elements 112A-112C of the dental tray 110 of FIG. 1. The imaging element 220 includes an illumination device 221 and a stereoscopic camera pair 222. Stereoscopic camera pairs may be advantageously allow multiple cameras in the tight space of the oral cavity given the constraints of stereo viewing angle (distance between the cameras relative to the distance to the object) and address the challenge of resolving details of the object.

The stereoscopic camera pair 222 includes a first camera 223A and a second camera 223B, each camera 223A-223B configured to generate an image of a section of the portion of the teeth at slightly different angles. In one embodiment, the stereoscopic camera pair 222 may be a Naneye stereo camera set produced by AWAIBA of Maderia, Portrugal.

The images generated by each stereoscopic camera pair may be used to generate a 3D image of the section of the portion of the teeth where the fields of view of the cameras overlap. Each of the two cameras 223A-223B captures an image of the same scene, but the cameras 223A-223B are separated by a known distance. The computing device 101 may compare the images to determine parts of the image that match, but are shifted between the images. The shifted amount is called the disparity and the disparity at which objects in the image best match is used by the computing device 101, along with the known separation distance of the cameras 223A-223B, to calculate the distance of the objects from the camera pair 222. The distance information may be used to generate 3D images from 2D images, and ultimately to generate a 3D model that includes the portion of teeth in the field of view of the camera pair 222. Because multiple camera pairs 222 are in fixed relative position to each other on the dental tray, the distance information may be used to stitch together 2D images from the two cameras in the camera pair to form a full 3D image of the patient's dentition with minimum computational complexity.

The illumination device 221 may include one or more light emitting devices. The illumination device 221 may include at least one of a light emitting device placed between the cameras 223A-223B of each camera pair 222 or beside the camera pair 222. The light emitting devices may include one or more of light emitting diodes (LEDs), optical fibers connected to a light source, incandescent filaments, or any other light producing element. The illumination device 221 may be positioned to illuminate a portion of teeth of patient in a field of view of the imaging element 220. In one embodiment, the imaging element 220 does not include an illumination device 221. However, an illumination device may be included in a dental tray separate from the imaging element 220. The illumination device 221 may provide uniform, random, or structured illumination. The illumination device 221 may include one or more of a white light source or a monochrome light source of one or more possible wavelengths or colors. The illumination devices 221 for different imaging elements 220 may be of different wavelengths to distinguish between different imaging elements 220.

Figure 2B:
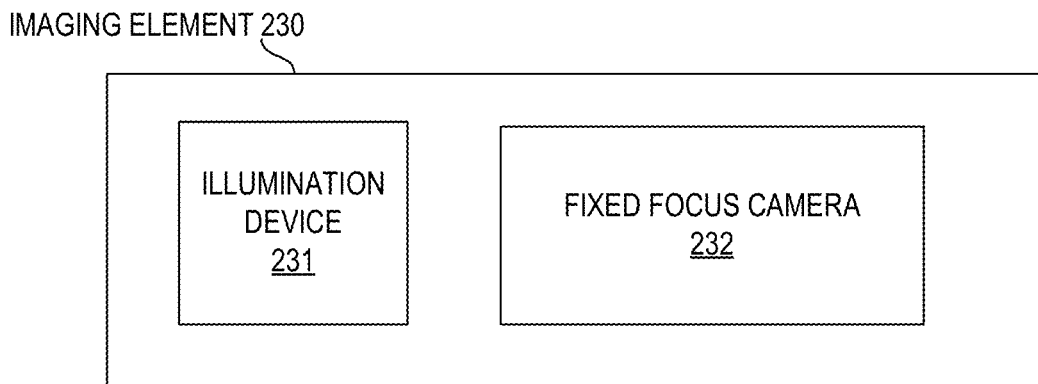
FIG. 2B illustrates one embodiment of an imaging element for generating images using a fixed focus camera.

FIG. 2B illustrates one embodiment of an imaging element 230 for generating images using a fixed focus camera 232. The imaging element 230 may be one of the array of imaging elements 112A-112C of the dental tray 110 of FIG. 1. The imaging element 230 includes an illumination device 231 and a fixed focus camera 232.

Like the illumination device 221 of the imaging element 220 of FIG. 2A, the illumination device 231 may include one or more light emitting devices and may be positioned to illuminate a portion of teeth of the patient in a field of view of the imaging element 230. In one embodiment, the imaging element 230 does not include an illumination device 231. In one embodiment, the illumination device 231 projects an illumination pattern onto the portion of the jaw such that weakly textured objects may be accurately modelled. The local blurring of the projected pattern as captured by the fixed focus camera 232 at each point may be used to determine the topography of the dental site.

The fixed focus camera 232 may be a camera with a focal length that is fixed throughout the image and, thus, a focus level that varies through the depth of interest. The fixed focus camera 232 may be configured to generate an image with embedded focus/defocus information that may be used to generate a 3D model of the portion of teeth in the field of view of the imaging element 230.

The computing device 101 may quantify the blur or defocus of the image at various points and determine the distance of an object at the point from the fixed focus camera 232 using the following formula:

$$\psi = \frac{2\pi}{\lambda}\left(\frac{1}{z_o^f} - \frac{1}{z_o'^f}\right)r^2,$$

where $\lambda$ is the wavelength of light, and $z_o^f$ and $z_o'^f$ are the in-focus and actual object distances from the fixed focus camera 232, respectively, and r is a measure of the aperture of the fixed focus camera 232.

In one embodiment, the fixed focus camera 232 takes multiple images at various focal lengths and the computing device 101 determines, for each of variety of points, the corresponding focal length at which the point is in focus. The distance of the object at the various points from the fixed focus camera 232 may be used as topography information to generate a 3D image of the portion of teeth in the field of view of the fixed focus camera 232. These 3D images generated from images taken by the fixed focus cameras may then be combined to create a 3D model of a patient's dentition. Because multiple cameras 232 may be in fixed relative position to each other on the dental tray, the distance information and known angles between cameras may be used to stitch together 3D images generated from the images captured by the fixed focus camera to form a full 3D model of the patient's dentition.

Figure 2C:
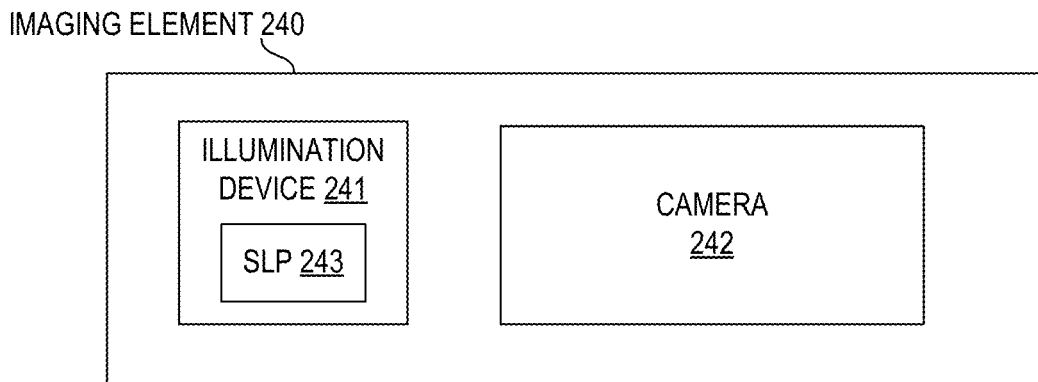
FIG. 2C illustrates one embodiment of an imaging element for generating images using a structured light projector.

FIG. 2C illustrates one embodiment of an imaging element 240 for generating images using a structured light projector 243. The imaging element 240 may be one of the array of imaging elements 112A-112C of the dental tray 110 of FIG. 1. The imaging element 240 includes an illumination device 241 and a camera 242.

Like the illumination device 221 of the imaging element 220 of FIG. 2A, the illumination device 241 may include one or more light emitting devices and may be positioned to illuminate a portion of teeth of patient in a field of view of the imaging element 240. The illumination device 241 includes a structured light projector 243 that projects a light pattern, such as a set of parallel lines, a grid, a pattern of dots, or any other known pattern, onto the portion of teeth in the field of view of the imaging element 240.

The camera 242 may be any camera that generates an image within a field of view. The camera 242 may be configured to generate an image of the portion of the teeth with the light pattern of the structure light projector 243 projected upon it. The image may be used to generate a 3D model of the portion of teeth in the field of view of the imaging element 240 using triangulation principles.

The computing device 101 may generate a 3D model of the portion of teeth in the field of view of the imaging element 240 by analyzing the deformation of the light pattern caused when striking surfaces to calculate the depth and surface information of the objects in the scene. For example, the intersections of a grid pattern may be spread out upon reflection from an object convexly shaped, protruding towards the camera 242 or bunched together upon reflection from an object concavely shaped, protruding away from the camera 242. Thus, the displacement of the intersections of a grid pattern upon reflection from an object may be used to determine the topology of the object or the distance of various points of the object to the camera 242. Each captured image may be a 2D image. However, the differences between the structured light pattern as captured in the captured image and the known original structured light pattern are usable to convert the 2D image into a 3D image. The 3D images from multiple cameras may then be stitched together based on known offsets and angles between the cameras to form a 3D model of a jaw and/or teeth of a patient.

In one embodiment, the structured light projector 243 projects a first light pattern onto the portion of the teeth and, subsequently, a second light pattern onto the portion of the teeth. The structured light projector 243 may include two structured light projectors, one for each light pattern, or may include a single structured light projector that projects different patterns. In particular, the first light pattern and the second light pattern may be different. For example, in one embodiment, the second light pattern is a shifted version of the first light pattern. In another embodiment, the first light pattern is a first grid having a first grid spacing and the second light pattern is a second grid having a second grid spacing that is different (e.g., larger or smaller) than the first grid spacing. By dynamically changing the phase or frequency of the pattern using sequence two different structured light projectors, ambiguities in the structural reconstruction can be resolved. Thus, a first image of a tooth captured with a first structured light pattern may be combined with a second image of the tooth captured with a second structured light pattern to improve the quality and resolution of a 3D image generated from the 2D images.

Figure 3A:
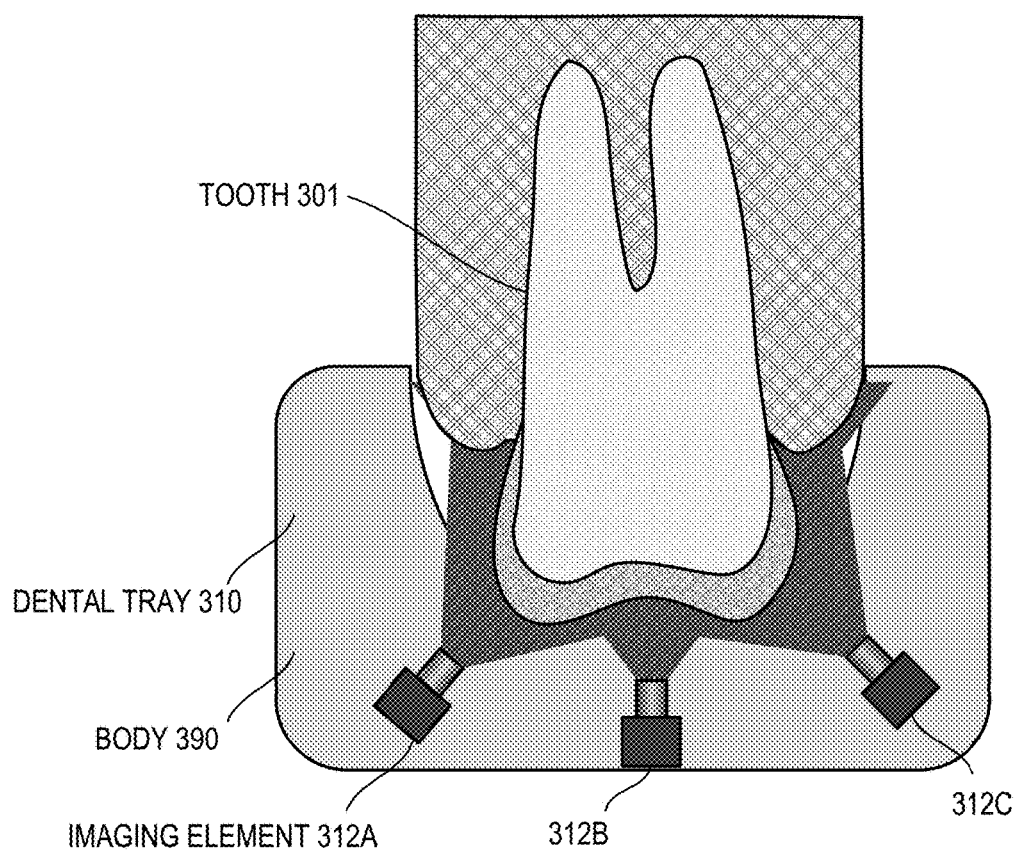
FIG. 3A illustrates a cross-sectional view of one embodiment of a dental tray.

FIG. 3A illustrates a cross-sectional view of one embodiment of a dental tray 310. The dental tray 310 includes, along a cross-section, three imaging elements 312A-312C embedded in the dental tray 310 and positioned to at least partially surround a tooth 301. The three imaging elements 312A-312C are encapsulated in a body 390, which may be a translucent material, such as polypropylene or another plastic, that can withstand disinfecting autoclave temperatures, and are positioned such that a first imaging element 312A has a field of view that includes a front of the tooth 301, a second imaging element 312B has a field of view that includes a bottom of the tooth 301, and a third imaging element 312C that includes a back of the tooth 301. The three imaging elements 312A-312C have overlapping fields of view such that the field of view of the first imaging element 312A overlaps with the field of view of the second imaging element 312B and the field of view of the second imaging element 312B overlaps with the field of view of the third imaging element 312C. The three imaging elements 312A-312C may be arranged such that their fields of view, together, include substantially all of the exposed portion of the tooth 301 (e.g., that is above the gum line).

Figure 3B:
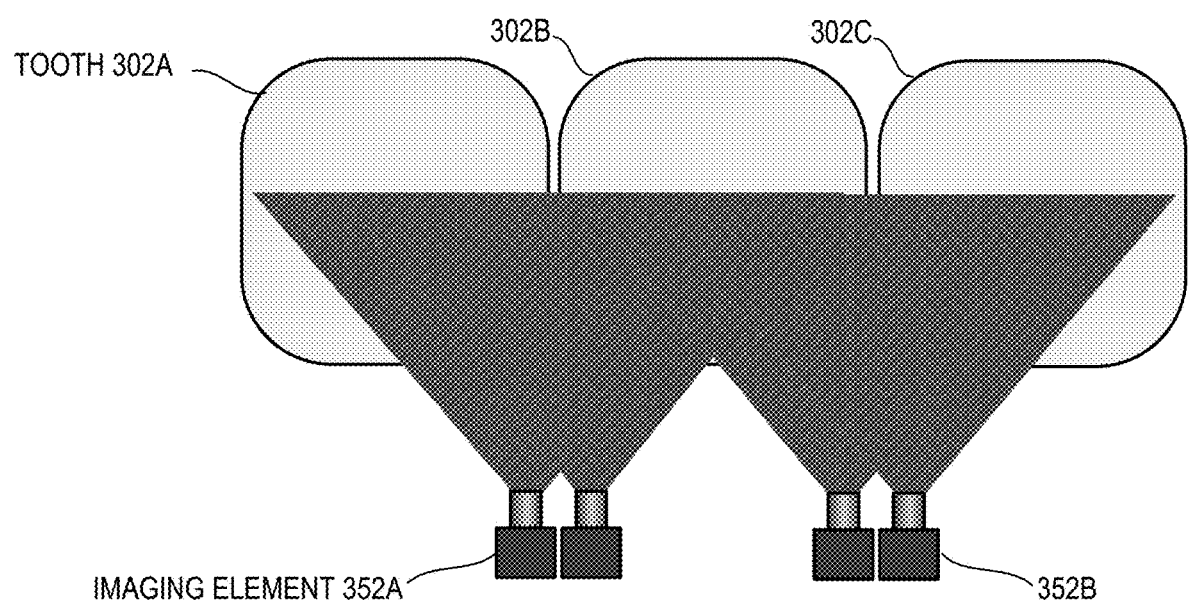
FIG. 3B illustrates a side view of one embodiment of an imaging element arrangement for a dental tray.

FIG. 3B illustrates a side view of one embodiment of an imaging element arrangement. The imaging elements 352A-352B (illustrated as stereoscopic camera pairs) are positioned to align with interproximal gaps between teeth 302A-302C. In other embodiments, each of the imaging elements 352A-352B may be aligned with a center of a tooth 302A-302C.

The imaging elements may be arranged, as illustrated in FIGS. 3A-3B, with sufficient overlap to cover the entire set of the patient's teeth corresponding to the tray segment size. Thus, the topography of all of the patient's teeth may be captured at once, using a single snapshot of all of the imaging elements at the same time. The positioning of the imaging elements may be tailored to correspond to the tooth geometry in the respective dental zones to reduce the number of imaging elements used in the dental tray. In particular, the spacing between imaging elements may be variable such that each tooth is captured by respective imaging elements.

Figure 3C:
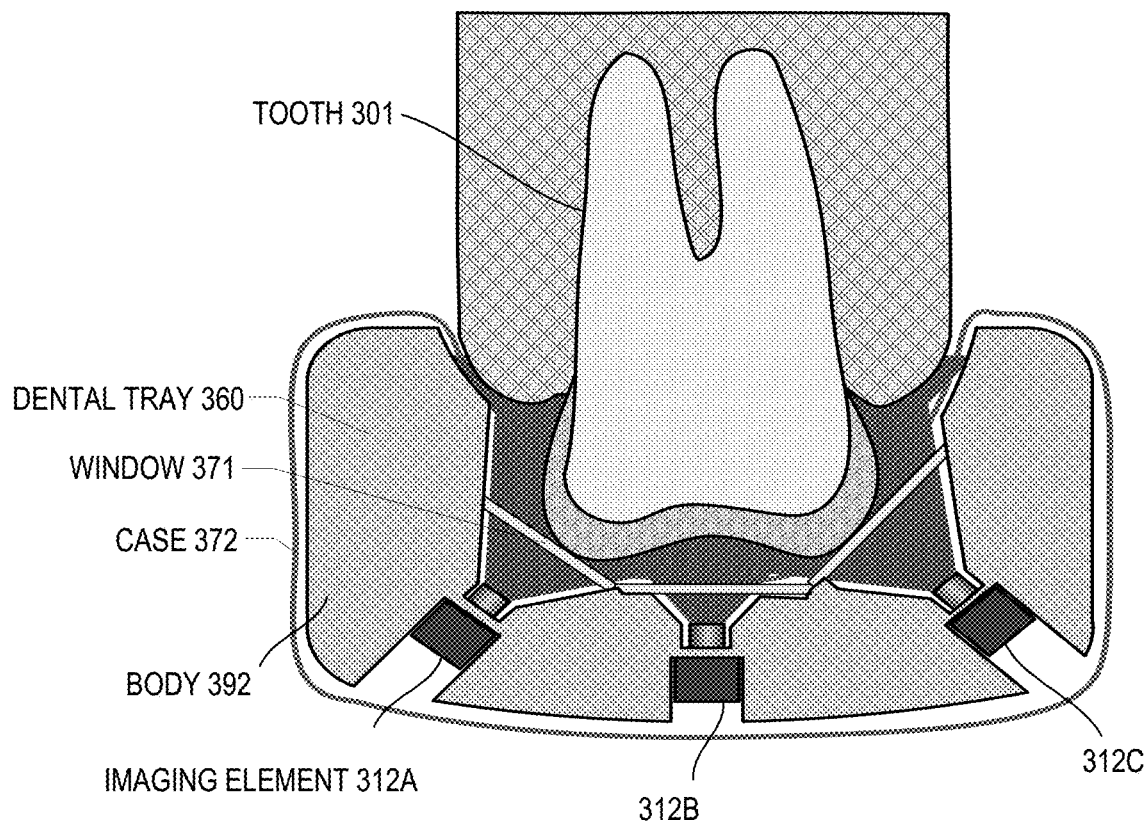
FIG. 3C illustrates a cross-sectional view of another embodiment of a dental tray.

FIG. 3C illustrates a cross-sectional view of another embodiment of a dental tray 360. The dental tray 360 includes, along a cross-section, three imaging elements 312A-312C embedded in a body 392 and positioned to at least partially surround a tooth 301. The imaging elements 312A-312C may be strategically retained in space by a rigid body 392 of minimal size. The dental tray 360 may be encased in a transparent case 372 that surrounds the dental tray 360. The case 372 may be disposable or autoclavable, saving the need to subject the imaging and illumination elements to the high autoclave temperatures. Whereas the case 372 may be transparent, the body 392 may be opaque with the exception of one or more windows 371 disposed between the imaging elements 312A-312C and the tooth 301.

Figure 4:
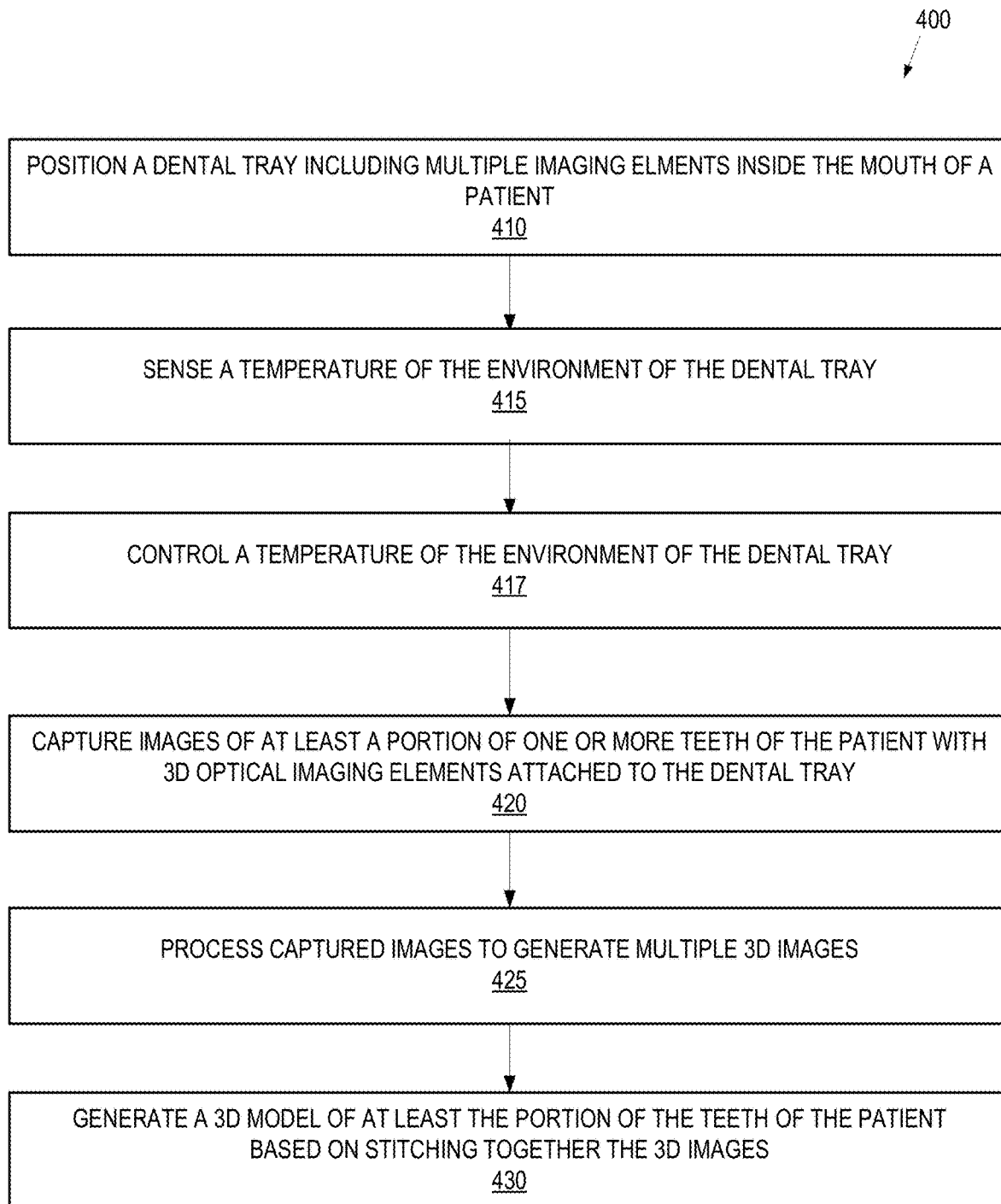
FIG. 4 illustrates a flow diagram for a method of generating a 3D model of teeth of a patient based on images captured by a dental tray, in accordance with embodiments of the present invention.

FIG. 4 illustrates a flow diagram for a method 400 of generating a 3D model of teeth of a patient, in accordance with embodiments of the present invention. The method 400 may be at least partially performed by processing logic that may comprise hardware (e.g., circuitry, dedicated logic, programmable logic, microcode, etc.), software (such as instructions run on a processing device), firmware, or a combination thereof. In one implementation, the method 400 may be at least partially performed by the system 100 of FIG. 1. For simplicity of explanation, the method 400 is depicted and described as a series of acts. However, acts in accordance with this disclosure can occur in various orders, concurrently, and/or with other acts not presented or described herein. Furthermore, not all illustrated acts may be required to implement the method 400 in accordance with the disclosed subject matter.

The method 400 begins at block 410 with the positioning of a dental tray, such as the dental tray 110 of FIG. 1, inside the mouth of a patient. Adjusting to different mouth sizes may be accomplished by providing a set of dental trays, each as described above, but of a different size. Thus, positioning the dental tray inside the mouth of the patient may include selecting a dental tray of an appropriate size from a set of dental trays of different sizes. The set of dental trays may include two, three, or more dental trays of different sizes.

The dental tray may be positioned to at least partially surround one or more teeth of the patient. In one embodiment, the patient bites down upon the dental tray to fix the position of the dental tray inside the patient's mouth while images are captured, as described below with respect to block 420.

At block 415, the temperature of the environment of the dental tray is sensed. The temperature may be sensed using one or more thermal sensors attached to the dental tray. At block 417, the processing logic controls the temperature of the environment of the dental tray, based on the sensed temperature, to defog the dental tray, preventing the generation of fog on the dental tray or removing fog that is present. The processing logic that controls the temperature of the dental tray may be integral with the dental tray or communicatively coupled to the dental tray. The processing logic may control the temperature by adjusting the settings of the imaging elements (e.g., intensity of illumination devices thereof) and/or heating elements to prevent the generation of fog and/or remove accumulated fog. In one embodiment, processing logic includes an ambient environment thermal sensor to sense the temperature of an environment of the dental tray (e.g., a temperature of a patient's oral cavity) and one or more additional thermal sensors to detect temperatures of the dental tray at one or more regions of the dental tray. Processing logic may set a temperature threshold based on the detected ambient temperature, and may adjust settings of the imaging elements and/or heating elements to cause the temperature at the one or more regions to approximately match the ambient temperature. Alternatively, or additionally, processing logic may include a preset temperature threshold (e.g., 98.6 degrees F.), and may adjust settings of the imaging elements and/or heating elements to cause the regions of the dental tray to reach the threshold temperature even before the dental tray is inserted into a patient's mouth.

At block 420, 3D optical imaging elements embedded or otherwise attached to the dental tray are used to capture images of at least a portion of the teeth of the patient. Because the dental tray may lack moving parts and be relatively static when the patient bites down on the tray, proper positioning may be achieved without use of a viewfinder. However, in one embodiment, one or more of the imaging elements may provide a real-time image to verify that the dental tray is well-seated before the imaging elements capture the images used to generate a 3D model. These images may be provided to a processing device for output to a display.

The 3D optical imaging elements may include imaging elements such as those described with respect to FIGS. 2A-2C and/or in an arrangement as described in FIGS. 3A-3B. In particular, the 3D optical imaging elements may include one or more light sources and/or one or more cameras. The 3D optical imaging elements may include one or more of a stereoscopic camera pair, a fixed focus camera, or a camera paired with a structured light projector.

The 3D optical imaging elements may be used to simultaneously capture images of various sections of the portion of teeth of the patient in a single snapshot, significantly reducing the amount of time used to generate enough data to model the teeth of the patient and reducing the possibility that the dental tray (and the 3D optical imaging elements thereof) may shift during capture. In one embodiment, each 3D optical imaging element or grouping of 3D optical imaging elements is used sequentially to capture an image of a section of the portion of teeth. The sequential triggering of the 3D optical imaging elements may be performed to reduce heat generation and/or the bandwidth used to transmit the images from the optical imaging elements to a computing device used to generate a 3D model of the teeth of the patient as described below with respect to block 430. In one embodiment, sets of two or more 3D optical imaging elements are used sequentially, each of the elements of the set being used simultaneously.

At block 425, the processing logic generates multiple 3D images based on the captured images (which may be captured two dimensional (2D) images with additional information usable to generate 3D images from the 2D images). The processing logic may generate a 3D image, e.g., an image including depth and/or topographic information, in a number of ways. In one embodiment, the processing logic generates a respective 3D image from the captured image or images from each imaging element. In one embodiment, the processing logic receives two images from each camera in a stereoscopic camera pair and generates a 3D image from the two images. The 3D image may be generated, as described above, by determining parts of the images that match, but are shifted between the images. The shifted amount is called the disparity and the disparity at which objects in the image best match may be used by the processing logic to calculate distance information of the 3D image. In one embodiment, the processing logic receives an image from a fixed focus camera configured such that the image focus level varies through the depth of interest, but not enough to result in a blurred image. The processing logic may quantify the blurring at various points on the image and generate depth information for the section of the portion of teeth in the field of view of the fixed focus camera based on the blurring. The distance of the blurred object point relative to the known focused object distance may be determined from the blur information by analyzing the point spread function at the object point. In particular, the further an object is from the in-focus plane, the more blurred it appears. The processing logic may use the amount of blurring to determine distance information of the 3D image. In one embodiment, the processing logic receives an image with a structured light pattern projected onto an object. The processing logic may use the amount of distortion of the light pattern introduced by the object to determine distance information of the 3D image.

At block 430, the 3D images generated are used to generate a 3D model of at least the portion of the teeth of the patient. The 3D model may be generated by stitching the 3D images together to generate a complete 3D model of at least of the portion of the teeth of the patient. The 3D images from different imaging elements using different imaging modalities may be combined together to generate a 3D model of at least the portion of the teeth of the patient. Stitching the 3D images together may be relatively straightforward given the relatively fixed positions of the 3D optical imaging elements with respect to each other. Each dental tray may be used in an initial calibration procedure in which stitching and other vision reconstruction parameters are derived by measuring a known 3D object using the dental tray.

Figure 5:
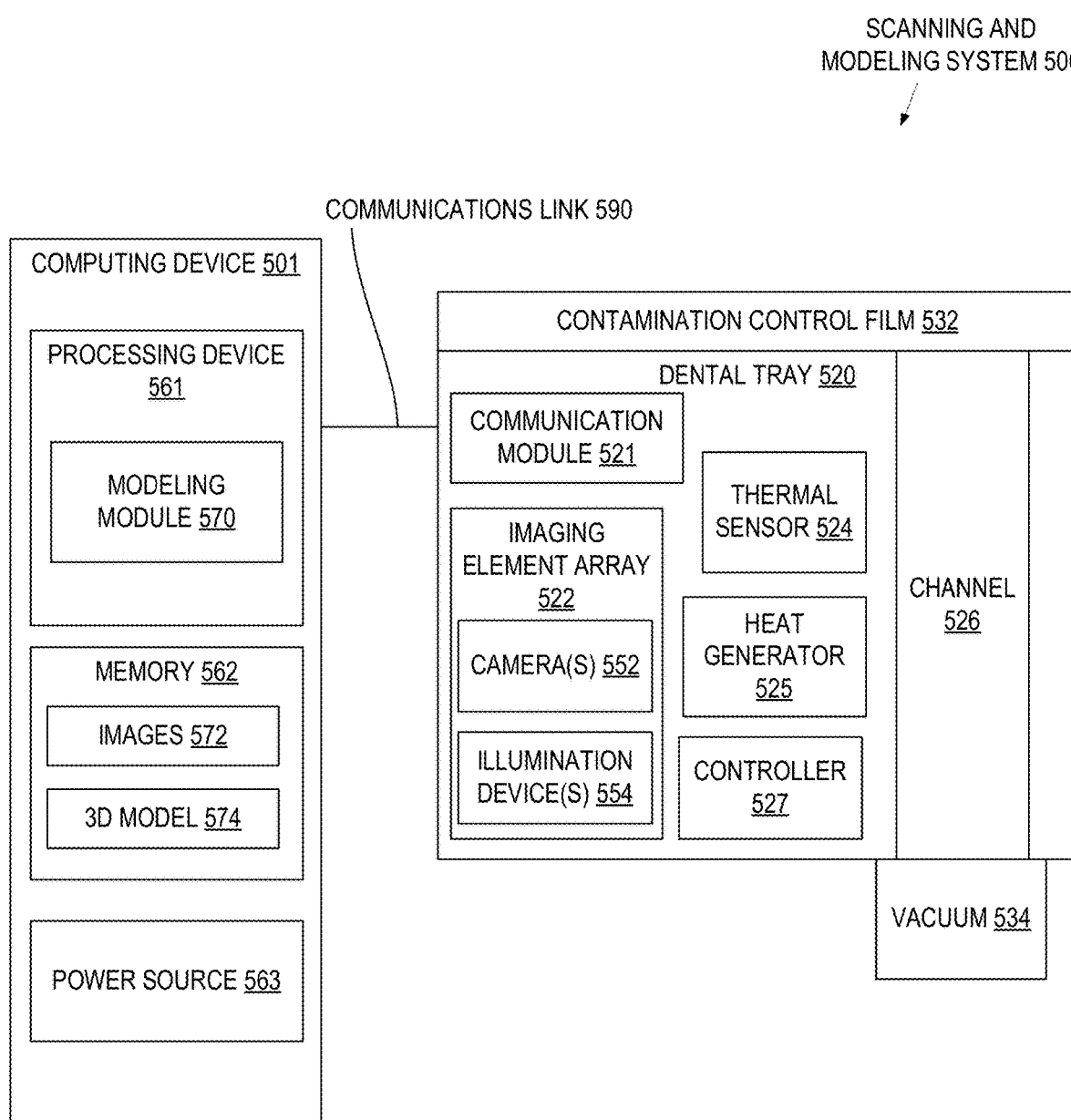
FIG. 5 illustrates a functional block diagram of an embodiment of a scanning and modeling system.

FIG. 5 illustrates a functional block diagram of an embodiment of an intraoral scanning and modeling system 500. The intraoral scanning and modeling system 500 includes a computing device 501 that generates a 3D model 574 of a patient's teeth based on images 572 captured by 3D optical imaging elements 522 embedded in or otherwise attached to a dental tray 520.

The dental tray 520 may be shaped to at least partially surround a plurality of teeth of a patient. In particular, the dental tray 520 may include an internal surface that at least partially surrounds the plurality of teeth of the patient. The dental tray 520 may surround all of the teeth of the patient, the upper or lower teeth of the patient, a quadrant of the teeth of the patient, or any other section of the teeth of the patient including two or more teeth.

The dental tray 520 has an array of three-dimensional (3D) optical imaging elements 522 embedded in or otherwise attached to the dental tray. The 3D optical imaging elements may each include an illumination device 554 configured to illuminate one or more of the plurality of teeth and a camera 552 configured to capture an image of the one or more of the plurality of teeth.

The camera 552 may be any image capturing device and may be configured to capture color images or black-and-white images. The camera 552 may be configured to capture optical information, including information outside the visible spectrum in the infrared and/or ultraviolet regions. The illumination device 554 may include one or more light emitting devices, which may include one or more of light emitting diodes (LEDs), optical fibers connected to a light source, incandescent filaments, or any other light producing element. The illumination device 554 may include one or more of a white light source covering at least the full visible spectrum range or a monochrome source. The illumination device 554 may, for example, include a red light source, a blue light source, and a green light source.

The array of 3D optical imaging elements 522 may be arranged such that a first one or more of the plurality of teeth to be imaged by a first 3D optical imaging element of the first plurality of 3D optical imaging elements at least partially overlaps with a second one or more of the plurality of teeth to be imaged by a second 3D optical imaging element of the first plurality of 3D optical imaging elements. The array of 3D optical imaging elements 522 may include two sets of 3D optical imaging elements, wherein the first set is configured to capture images of the upper teeth of the patient and the second set is configured to capture images of the lower teeth of the patient.

In one embodiment, the 3D optical imaging elements 522 include a structured light projection optical imaging element that includes, as an illumination device 554, a structured light projector configured to project a light patent onto one or more of the plurality of teeth, and a camera 552. The structured light projection optical imaging element may include, as an illumination device 554, two structured light projectors, each configured to project a different light pattern onto the one or more of the plurality of teeth, or a single light projector configured to project two different light patterns onto the one or more of the plurality of teeth. The first light pattern may be a first grid having a first grid spacing and the second light pattern is a second grid having a second grid spacing that is different that the first grid spacing.

In one embodiment, the 3D optical imaging elements 522 include a stereoscopic optical imaging element that includes, as a camera 552, a stereoscopic pair of cameras configured to capture images of one or more of the plurality of teeth from slightly different angles, and an illumination device 554. In one embodiment, the 3D optical imaging elements 522 include a depth-from-defocus optical imaging element that includes, as a camera 552, a fixed focus camera with a fixed focal length and, thus, a focus level that varies through the depth of interest, and an illumination device 552.

The dental tray 520 may include a communication module 521 that transmits images captured by the imaging elements 522 to the computing device 501 via a communications link 590. The communication module 521 may also be configured to receive information, such as information to control the imaging elements 522, from the computing device 501 over the communications link 590.

In one embodiment, the communication module 521 is a wired communication module. The communication module 521 may be a network adapter, a universal serial bus (USB) module, a serial communication module, a parallel communication module, and so on. The communication module 521 may transmit the captured images over a wired communications link 590.

In one embodiment, the communication module 521 is a wireless module that establishes a wireless communications link 590 with the computing device 501. In one embodiment, the wireless module is configured to communicate using Bluetooth. Alternatively, the wireless module may be configured to communicate using Wi-Fi, Zigbee, Internet Protocol version 6 over Low power Wireless Area Networks (6LowPAN), power line communication (PLC), or other communication protocols. The wireless module may include a processing device, a memory and/or a network adapter. The processing device of the wireless module may be a microcontroller, a digital signal processor (DSP), a programmable logic controller (PLC), a microprocessor or programmable logic device such as a field programmable gate array (FPGA) or a complex programmable logic device (CPLD). The memory of the wireless module may include a non-volatile memory (e.g., RAM) and/or a volatile memory (e.g., ROM, Flash, etc.). In one embodiment, the memory is integrated into the processing device of the wireless module.

The dental tray 520 may be coupled to or include a thermal sensor 524 that senses a temperature of an environment of the dental tray 520. The sensed temperature may be transmitted, using the communication module 521 via the communications link 590, to the computing device 501. The computing device 501, or the processing device 561 thereof may control the temperature of the environment of the dental tray 520 based on the sensed temperature to defog the dental tray 520, either preventing the formation of fog on the dental tray 520 or removing fog that is present. Alternatively, dental tray 520 may include a controller 527 that receives the temperature information and controls the temperature of the environment of the dental tray 527. The controller 527 may be a microcontroller, a digital signal processor (DSP), a programmable logic controller (PLC), a microprocessor or programmable logic device such as a field programmable gate array (FPGA) or a complex programmable logic device (CPLD).

The computing device 501 or controller 527 may control the temperature of the environment of the dental tray 520 in a number of ways. In one embodiment, the computer device 501 or controller 527 controls one or more illumination devices 554 of the imaging elements 522 to generate heat to defog the dental tray 520. In one embodiment, the computer device 501 or controller 527 controls one or more heat generators 525 (also referred to as heating elements) embedded in or otherwise attached to the dental tray to generate heat in the environment of the dental tray 520.

The dental tray 520 may have one or more channels 526 through the dental tray between an internal surface of the dental tray 520 and a vacuum port of an external surface of the dental tray 520. A disposable and optically clear contamination control film 532 may be disposed over the internal surface of the dental tray prior to insertion of the dental tray into the mouth of the patient for intraoral scanning. The film 532 may be a thin film (e.g., approximately 0.4-0.6 millimeters thick) composed of polyvinyl chloride, polyethylene, or any other material. A vacuum machine 534 may be coupled to the vacuum port to remove air from the channels 526 and adhere the film 532 to the internal surface of the dental tray.

In one embodiment, the dental tray 520 is composed of or encased in a translucent material that can withstand disinfecting autoclave temperatures and the imaging elements 522 and other components are embedded within the dental tray 520. The dental tray 520 may be composed of or encased in an autoclavable material that is not damaged or deformed by temperatures between approximately 100° C. and 150° C. For example, the dental tray 520 may be composed of or encased in polypropylene or another translucent plastic.

The computing device 501 may include a processing device 561 that executes a modelling module 570. The modelling module 570 may take, as input, images 572 received from the imaging elements 522 and generate a 3D model 574 of a dental site (e.g., of an upper and lower jaw and teeth) based on the received captured images 572. The 3D model 574 may be based on color images and, therefore, be a color 3D model. The color 3D model may be used for display, interpretation, and tooth-shading purposes to ensure that prosthetics match the natural color of the patient's teeth.

The images 572 and the resulting 3D model 574 may be stored in a memory 574 of the computing device 501. The computing device 501 may also include a power source 563 that provides power to the computing device and/or provides power (e.g., over the communications link 590 which may also act as a power link) to the components of the dental tray 520, such as the imaging elements 522. Alternatively, the dental tray 520 may include its own power source (not shown), which may be a rechargeable battery, or be connected to power source separate from the computing device 501.

The images 572, in addition to being used to generate the 3D model 574, may be used for dental hygiene diagnosis. A dental practitioner may view the images 572 remotely from the patient to develop a dental hygiene treatment plan that may be incorporated into a comprehensive treatment plan. In one embodiment, computer software analyzes the images to generate a dental hygiene diagnosis, expanding the access of patients to treatment initializing diagnoses.

Figure 6:
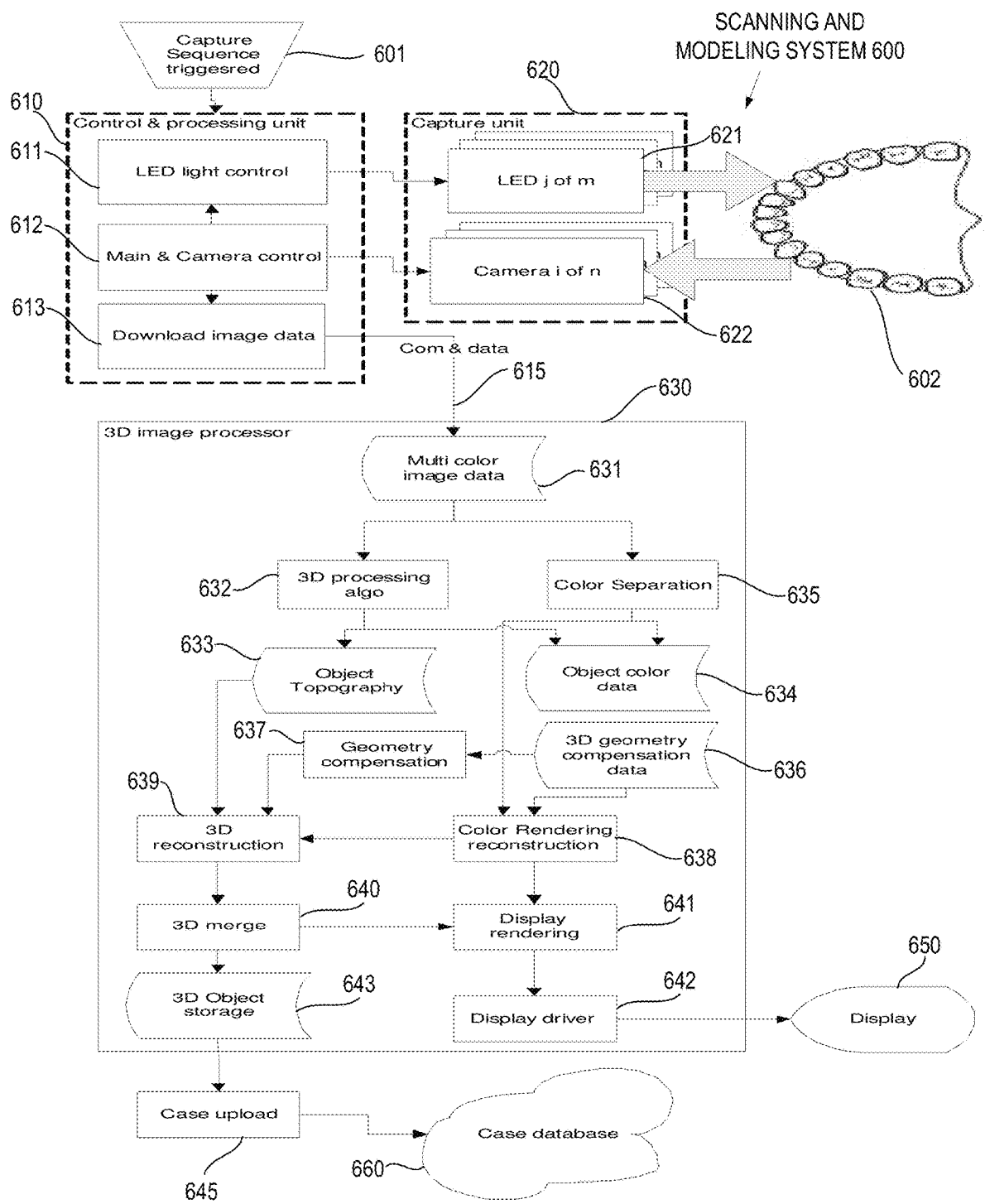
FIG. 6 illustrates a functional block diagram of another embodiment of a scanning and modeling system.

FIG. 6 illustrates a functional block diagram of an embodiment of an intraoral scanning and modeling system 600. In response to a command triggering a capture sequence 601, a control and processing unit 601 controls a capture unit 620 to perform a capture sequence and capture one or more images of a patient's mouth 602. The control and processing unit 610 may correspond to and perform at least some of the functions of the computing device 501 of FIG. 5 and the capture unit 620 may correspond to and have at least some of the features of the dental tray 520 of FIG. 5. For example, the capture unit 620 may include or be a component of a dental tray, such as an imaging element 112A-112C of dental tray 110 of FIG. 1. Alternatively, capture unit 620 may be a dental tray, such as dental tray 110 of FIG. 1.

The control and processing unit 610 may include an LED light control module 611 that controls one or more LED lights 621 of the capture unit 620 and may also include a main and camera control module 612 that controls one or more cameras 622 of the capture unit 620. The control and processing unit 610 may include an image data module 613 that sends communications, such as image data, via a communications bus 615 to a 3D image processor 630. The 3D image processor 630 may also correspond to and perform at least some of the functions of the computing system 501 of FIG. 5.

The 3D image processor 630 may receive data including multiple color images 631. The 3D image processor 630 may include a 3D processing algorithm module 632 that performs one or more 3D processing algorithms, such as those described above with respect to FIGS. 2A-2C, to generate object topography data 633 and object color data 634 from the multiple color images 631. The object color data 634 may also be at least partially generated by a color separation module 635 that derives object color information from the received color images 631.

The 3D image processor may include 3D geometry compensation data 636 derived from an initial calibration of the capture unit 620 as described above. The 3D geometry compensation data 636 may include, for example, stitching and other vision reconstruction parameters. The 3D geometry compensation data 636 may further include color compensation data that is used, along with the object color data 634 to perform a color rendering reconstruction by a color rendering reconstruction module 638. The 3D geometry compensation data 636 may be used by a geometry compensation module 637 to perform geometry compensation that, among other things, may standardize the images based on the relative positions of the cameras 622 within the capture unit 620.

The geometry compensation may be used, along with the object topography data 633 by a 3D reconstruction module 639 to perform 3D reconstruction. The color rendering reconstruction performed by the color rendering reconstruction module 638 may also be used to assist in the 3D reconstruction performed by the 3D reconstruction module 639.

The result of the 3D reconstruction may be used by a 3D merge module 640 to perform a 3D merge and generate a 3D model of the patient's mouth 602. The results of the 3D merge and the results of the color rendering reconstruction may be used by a display rendering module 641 to render a color display of the model of the patient's mouth 602. The rendering may be fed to a display driver 642 of the 3D image processor 630 which drives a display 650 to present a user with a color display of the model of the patient's mouth 602.

The 3D merge may result in a storable 3D object 643 that may be uploaded by a case upload module 645, e.g., a network interface, to a case database 660, where the 3D object 643 of the model of the patient's mouth 602 is stored in association with information about the patient.

Figure 7:
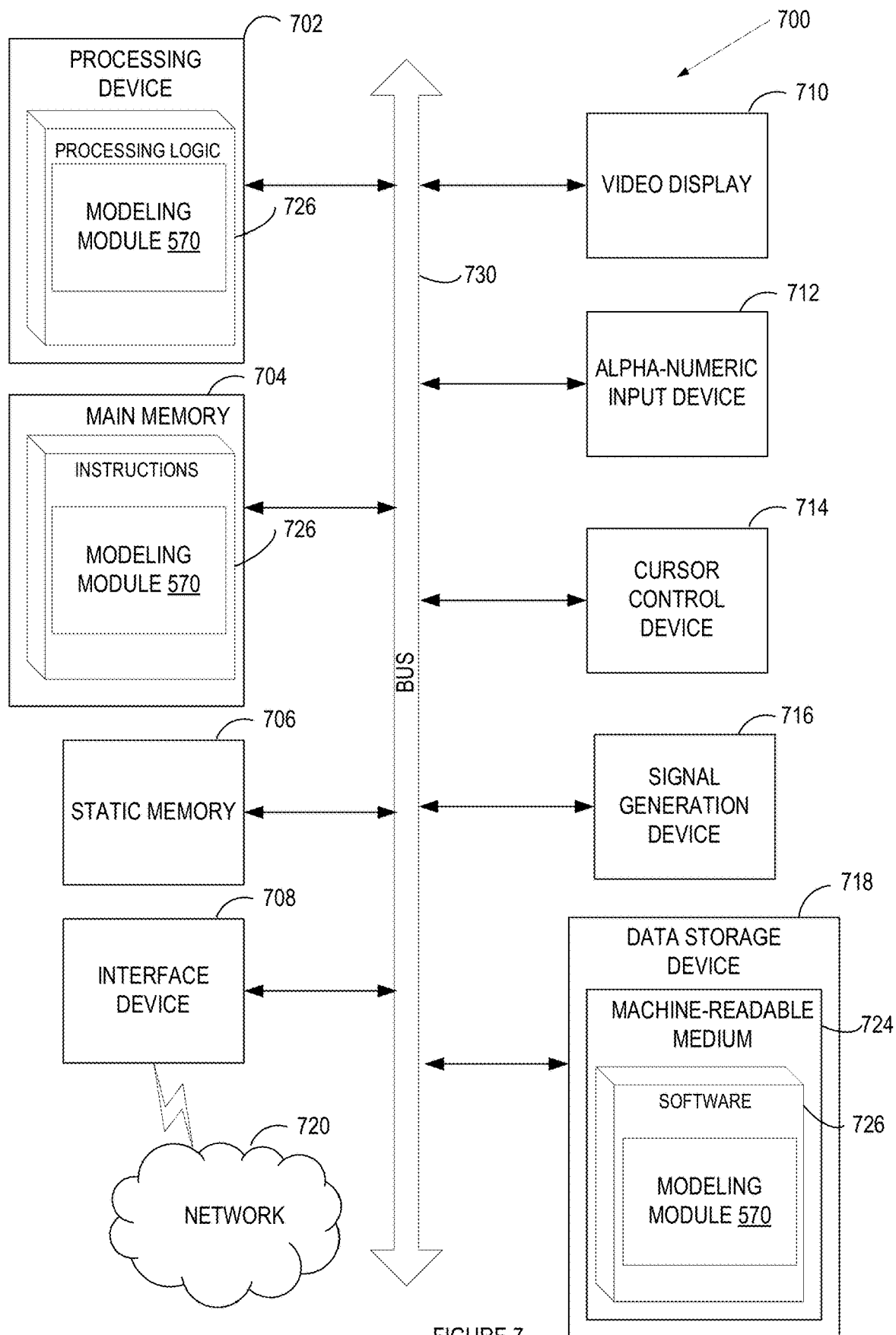
FIG. 7 illustrates a block diagram of an example computing device, in accordance with embodiments of the present invention.

FIG. 7 illustrates a block diagram of an example computing device, in accordance with embodiments of the present invention. In alternative implementations, the machine may be connected (e.g., networked) to other machines in a LAN, an intranet, an extranet, or the Internet. The machine may operate in the capacity of a server or a client device in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 700 includes a processing device 702, a main memory 704 (e.g., read-only memory (ROM), flash memory, dynamic random access memory (DRAM) (such as synchronous DRAM (SDRAM) or DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 may be configured to execute the processing logic 726 for performing the operations and steps discussed herein.

The computer system 700 may further include an interface device 708 (e.g., a network adapter, wireless module, etc.) communicably coupled to a network 720 and/or to a dental tray. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), and a signal generation device 716 (e.g., a speaker).

The data storage device 718 may include a machine-accessible storage medium 724 on which may be stored software 726 embodying any one or more of the methodologies of functions described herein. The software 726 may also reside, completely or at least partially, within the main memory 704 as instructions 726 and/or within the processing device 702 as processing logic 726 during execution thereof by the computer system 700; the main memory 704 and the processing device 702 also constituting machine-accessible storage media.

The machine-readable storage medium 724 may also be used to store instructions 726 to implement the modeling module 570 and/or any one or more of the methodologies of functions described herein in a computer system, such as the system described with respect to FIG. 1, and/or a software library containing methods that call the above applications. While the machine-accessible storage medium 724 is shown in an example implementation to be a single medium, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that may be capable of storing, encoding or carrying a set of instruction for execution by the machine and that cause the machine to perform any one or more of the methodologies of the disclosure. The term "machine-accessible storage medium" shall accordingly be taken to include, but not be limited to, solid-state memories, and optical and magnetic media.

In the foregoing description, numerous details are set forth. It may be apparent, however, that the disclosure may be practiced without these specific details. In some instances, well-known structures and devices are shown in block diagram form, rather than in detail, in order to avoid obscuring the disclosure.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "performing", "creating", "registering", "applying", "allocating", "merging", "using", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may comprise a general purpose computer selectively activated or reconfigured by a computer program stored in the computer. Such a computer program may be stored in a machine readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems may appear as set forth in the description below. In addition, the disclosure is not described with reference to any particular programming language. It may be appreciated that a variety of programming languages may be used to implement the teachings of the disclosure as described herein.

The disclosure may be provided as a computer program product, or software, that may include a machine-readable medium having stored thereon instructions, which may be used to program a computer system (or other electronic devices) to perform a process according to the disclosure. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), etc.

Whereas many alterations and modifications of the disclosure may no doubt become apparent to a person of ordinary skill in the art after having read the foregoing description, it is to be understood that any particular example shown and described by way of illustration is in no way intended to be considered limiting. Therefore, references to details of various examples are not intended to limit the scope of the claims, which in themselves recite only those features regarded as the disclosure.

What is claimed is:

1. A system comprising:
    a dental tray shaped to at least partially surround a plurality of teeth of a dental arch;
        a first array of fixed focus cameras attached to the dental tray, wherein each fixed focus camera in the first array of fixed focus cameras is a camera with a focal length that is fixed throughout an image, wherein each fixed focus camera of the first array of fixed focus cameras has a fixed position and orientation relative to one or more other fixed focus camera of the first array of fixed focus cameras, the first array of fixed focus cameras configured to generate a plurality of images of the plurality of teeth of the dental arch; and
    a processing device to:
    receive the plurality of images;
        stitch the plurality of images together based on calibration data specifying predetermined image stitching parameters for combining the plurality of images, wherein the predetermined image stitching parameters are based on predetermined fixed relative positions and orientations of fixed focus cameras from the first array of fixed focus cameras; and
    generate a three-dimensional model of the plurality of teeth based on the stitched plurality of images.

2. The system of claim 1, further comprising:
    a controller for the dental tray, the controller to activate the first array of fixed focus cameras to cause the first array of fixed focus cameras to generate the plurality of images.

3. The system of claim 2, further comprising:
    one or more heating elements;
    wherein the controller is further to activate the one or more heating elements to cause the one or more heating elements to heat the dental tray to a temperature that mitigates fogging of the first array of fixed focus cameras.

4. The system of claim 3, wherein the one or more heating elements comprise one or more optical heating elements that are to optically heat the dental tray.

5. A system comprising:
    a dental tray shaped to at least partially surround a plurality of teeth of a dental arch;
    a first array of cameras attached to the dental tray, wherein each camera of the first array of cameras has a fixed position and orientation relative to one or more other camera of the first array of cameras, the first array of cameras configured to generate a plurality of images of the plurality of teeth of the dental arch;
    one or more heating elements;
    a first thermal sensor to detect a first temperature of the dental tray;
    a second thermal sensor to detect a second temperature of an oral cavity;

a controller to:
  determine that the first temperature of the dental tray is lower than the second temperature of the oral cavity;
  activate the one or more heating elements to cause the one or more heating elements to heat the dental tray;
  adjust the first temperature of the dental tray to cause the first temperature of the dental tray to increase towards the second temperature of the oral cavity using the one or more heating elements to heat the dental tray to a temperature that mitigates fogging of the first array of cameras; and
  activate the first array of cameras to cause the first array of cameras to generate the plurality of images; and
a processing device to:
  receive the plurality of images;
  stitch the plurality of images together based on calibration data specifying predetermined image stitching parameters for combining the plurality of images, wherein the predetermined image stitching parameters are based on predetermined fixed relative positions and orientations of cameras from the first array of cameras; and
  generate a three-dimensional model of the plurality of teeth based on the stitched plurality of images.

6. The system of claim 1, wherein a first field of view of a first fixed focus camera of the first array of fixed focus cameras overlaps with a second field of view of a second fixed focus camera of the first array of fixed focus cameras by a predetermined amount.

7. The system of claim 1, further comprising a second array of fixed focus cameras attached to the dental tray, wherein the first array of fixed focus cameras is configured to capture images of an upper section of the plurality of teeth and the second array of fixed focus cameras is configured to capture images of a lower section of the plurality of teeth.

8. The system of claim 1, wherein the dental tray comprises one or more channels through the dental tray between an internal surface of the dental tray and an external vacuum port, and wherein a vacuum is to couple to the external vacuum port to remove air from the one or more channels and adhere an optically clear disposable contamination control film to the internal surface of the dental tray.

9. The system of claim 8, wherein the one or more channels are to apply the vacuum at a plurality of locations on the internal surface of the dental tray, the vacuum having sufficient suction to secure the optically clear disposable contamination control film to the internal surface of the dental tray without tearing the optically clear disposable contamination control film, wherein the optically clear disposable contamination control film does not impact imaging quality or geometry of the plurality of images captured by the first array of fixed focus cameras.

10. The system of claim 1, wherein a first fixed focus camera of a first array of fixed focus cameras is configured to capture a color image.

11. The system of claim 1, wherein the dental tray comprises an autoclavable translucent material.

12. The system of claim 11, wherein the dental tray further comprises:
  a thermal sensor to sense a temperature of an environment of the dental tray; and
  a controller to control the temperature of the environment of the dental tray based on the sensed temperature to defog the dental tray.

13. The system of claim 1, further comprising:
  a plurality of light emitting devices to illuminate the plurality of teeth.

14. The system of claim 13, wherein the plurality of light emitting devices are configured to emit one or more wavelength of light having one or more illumination pattern onto the plurality of teeth.

15. The system of claim 1, wherein the processing device is to:
  quantify an amount of blur for points on an image generated by a fixed focus camera of the first array of fixed focus cameras; and
  determine depth values for the points based on the amount of blur for the points.

16. The system of claim 1, wherein two or more fixed focus cameras of the first array of fixed focus cameras are activated sequentially, and wherein sequential activation of the two or more fixed focus cameras reduces heat generation for the dental tray.

17. A method of generating a three-dimensional model of a dental arch based on images generated by an array of fixed focus cameras of a dental tray, the method comprising:
  receiving a plurality of images from a dental tray positioned to at least partially surround a plurality of teeth of a dental arch, the plurality of images having been generated by an array of fixed focus cameras attached to the dental tray, wherein each fixed focus camera in the array of fixed focus cameras is a camera with a focal length that is fixed throughout an image, and wherein each fixed focus camera of the array of fixed focus cameras has a fixed position and orientation relative to one or more other fixed focus camera of the array of fixed focus cameras;
stitching the plurality of images together based on calibration data specifying predetermined image stitching parameters for combining the plurality of images, wherein the predetermined image stitching parameters are based on predetermined fixed relative positions and orientations of fixed focus cameras from the array of fixed focus cameras; and
  generating a three-dimensional model of the plurality of teeth based on the stitched plurality of images.

18. The method of claim 17, wherein a first field of view of a first fixed focus camera of the array of fixed focus cameras overlaps with a second field of view of a second fixed focus camera of the array of fixed focus cameras by a predetermined amount.

19. The method of claim 17, further comprising:
  for each image of the plurality of images, quantifying an amount of blur for points on the image; and
  determining depth values for the points based on the amount of blur.

20. The method of claim 17, further comprising:
  sequentially activating two or more fixed focus cameras of the array of fixed focus cameras to reduce heat generation for the dental tray.

* * * * *